United States Patent [19]

Abyzov

[11] Patent Number: 5,445,537
[45] Date of Patent: Aug. 29, 1995

[54] STRAIN RELIEF COUPLING ASSEMBLY FOR AN ELECTRODE

[75] Inventor: Alex Abyzov, Brookline, Mass.

[73] Assignee: SRC Associates, Inc., Marblehead, Mass.

[21] Appl. No.: 332,395

[22] Filed: Oct. 31, 1994

[51] Int. Cl.⁶ ............................................. H01R 13/58
[52] U.S. Cl. ................................... 439/449; 439/909; 128/639; 128/641
[58] Field of Search ......................... 128/639, 640, 641; 607/115, 149, 152, 153; 439/909, 859, 371, 373, 449, 450, 451

[56] References Cited

U.S. PATENT DOCUMENTS

| | | | |
|---|---|---|---|
| 3,838,383 | 9/1974 | Wilbur et al. | 439/371 |
| 3,977,392 | 8/1976 | Manley . | |
| 3,993,049 | 11/1976 | Kater | 128/640 |
| 4,209,020 | 6/1980 | Nielsen . | |
| 4,357,063 | 11/1982 | Gray | 439/371 |
| 4,503,860 | 3/1985 | Sams et al. . | |
| 4,579,120 | 4/1986 | MacGregor . | |
| 4,706,680 | 11/1987 | Keusch et al. | 128/640 |
| 4,757,817 | 7/1988 | Healy . | |
| 4,865,566 | 9/1989 | Rosmussen | 128/639 |
| 5,199,432 | 4/1993 | Quedens et al. | 439/909 |
| 5,354,321 | 10/1994 | Burger | 807/115 |
| 5,355,883 | 10/1994 | Ascher | 128/641 |

OTHER PUBLICATIONS

3M Red Dot TM Electrodes Advertisement Brochure.
Medi-Trace ® S'Offset TM, and Offset TM Dx ECG Electrodes Advertisement Brochure.
Carbo Cone ® Monitoring Electrode Advertisement Brochure.

Primary Examiner—Lee S. Cohen
Assistant Examiner—Brain M. Green
Attorney, Agent, or Firm—Lappin & Kushmer

[57] ABSTRACT

A strain relief coupling assembly is disclosed for use for connecting a living body with medical monitoring device which records electrical signals generated by the body. The present invention provides mechanical separation between an adhesive pregelled electrode attached to the skin of the patient and an electrical lead transmitting signals to the monitoring device. The assembly thus reduces disturbances of the skin-to-gel contact site caused by the patient's movements, and results in a minimized noise component of recorded signals, effectively improving the quality of recorded traces for monitoring or measurement.

13 Claims, 2 Drawing Sheets

STRAIN RELIEF COUPLING ASSEMBLY FOR AN ELECTRODE

The present invention relates to the field of electrode assemblies for measurement of electrical signals generated by a living body, and more particularly to an improvement in measurement of such signals for medical purposes.

BACKGROUND OF THE INVENTION

Diagnosis of serious medical conditions has been greatly facilitated by use of medical monitoring devices which can be attached to living bodies through electrodes and which generate graphical representations, or traces, of the electrical signals generated by the body or by specific organs within the body. Such traces are characteristic of the physiological state of the living body or of the specific organ being studied, and they reveal important information to the physician or veterinarian regarding a patient's normal or abnormal medical condition in a non-invasive manner. Many kinds of traces are currently in use, for example, electrocardiograms, electroencephalograms, fetal monitoring devices, and the like.

Generally, these electrical monitoring devices function by physical attachment of an electrode to the skin of the patient, often in the vicinity of the organ to be studied. In the context of the invention, an electrode is an electrical conductor, such as a wire or lead used to establish electrical contact with a non-metallic portion of a circuit, for example, the skin of the patient. For use with electrical monitoring devices, an end of the wire or lead forming a conventional electrode may be releasably attached to an electrode coupling assembly, where the electrical coupling assembly includes an adhesive end which is attached to the patient, in a manner capturing an electrically conductive gel against the skin of the patient. The assembly further includes one portion, typically the male portion, of an electrical connector which is in direct electrical contact with the gel. The other portion of the connector is attached to the end of the electrode-to-be-attached. With this configuration, conductive attachment to the skin is effected by the electrically conductive gel. The wire of the electrode is releasably coupled to the gel through the connector portions, and thus to the monitoring device at the other end of the wire, creating an electrical circuit path from the skin through gel through the connector portions and through the wire to a monitoring device. The trace is generated by the monitoring device, typically in response to sensed conductivity between the skin at the gel-skin interface and another electrode connection to the patient.

Traces generated in this manner are representative of such electrical signals, but also include noise components, making it difficult to measure or monitor the desired parameter. Such noise may be due to a number of factors and sources, but a primary source is the patient's movements. Such movements typically disturb the electrical connections in the electrode coupling assembly described above. In particular, the attachment of the electrode via its connector to the electrical coupling assembly places a load force (due to weight of the electrode wire itself, for example) on the connector portion of the electrode coupling assembly, which is coupled to the gel. As the patient moves, causing reorientation of the coupling assembly, the load force on the gel varies accordingly. In response, the electrical conductivity of the gel between the connector and skin varies, resulting in a noise component added to the monitored electrical signal. Also, noise is generated by changes in electrical conductivity resulting from relative motion of the portions of the connector. For example, patients may pull on the electrode wire or scratch at the site of the adhesive attachment to the skin. If a small monitoring device is being used, it may temporarily hang from the wire. All of these events may cause strain on the connecting wire and resulting electrical noise. Noise interference created by the patient's movements can be especially problematic when the patient is ambulatory, for example, when the monitoring device is attached for an extended period of time to obtain a trace over time of an organ's electrical activity and the patient is allowed to move about or to go home. Strain on the electrode wire is common in traces of ambulatory patients. Traces generated for veterinary purposes are particularly subject to noise interference caused by patient movement.

The problem of spurious signals generated by relative movement between the connector portions has been recognized in the past. Medical practitioners have attempted to minimize movement of the connector portions by taping the end of the electrode near its connector portion to the patient, providing a measure of strain relief. However, this limits the ease of use since removal is difficult, and additionally, the adhesive tape itself can be a source of discomfort and inconvenience to the patient.

There have been prior art attempts at minimizing such noise, for example as disclosed in U.S. Pat. No. 4,757,817. In that patent, a single electrode connection pad is disclosed which includes both an aperture for application of the conductive gel and a connector portion for receiving an electrode connector and wire extending from a monitoring device. In U.S. Pat. No. 4,757,817, the pad is slit to establish an adhesive-backed flap used to secure the electrode wire to the pad, establishing a measure of strain relief. However, the slitted pad of U.S. Pat. No. 4,757,817 is a unitary structure and does not provide any physical separation between the strain relief feature point and the gel-bearing electrode-to-skin coupling.

U.S. Pat. No. 4,209,020 discloses a fetal monitoring electrode assembly with a single contact pad which establishes electrical contact with the mother's skin through an aperture under a connector element and which is directly attached to the monitoring device. Separate electrodes are attached to the fetus. The contact pad of U.S. Pat. No. 4,209,020 is affixed to the mother's thigh, thus purportedly minimizing movement of the fetal electrodes relative to the monitoring device. However, with a single pad housing both the electrode-to-skin coupling (gel) and the connection to the electrode wire, movement in either the fetus or the wire changes the shape of the gel, resulting in noise.

U.S. Pat. No. 4,503,860 discloses an adhesively attached pad in a serial arrangement with a connector arranged for releasable coupling to a primary electrode coupling device. That pad functions to stabilize an electrode in the vicinity of the measuring point and to relieve strain on the lead at its point of connection to the electrode proper. The anchor means of U.S. Pat. No. 4,503,860 is located a short distance away from the electrode. However, the anchor pad is integrated with the electrode lead and connector, so that each time the electrode is to be connected or disconnected, the primary electrical coupling device must be disturbed, resulting in a change in position of that coupling device and introducing measurement error.

In the electrode of U.S. Pat. No. 3,977,392, an aperture containing the conductive gel is separated from the male snap on a single adhesive pad by a flexible conductor which is purported to prevent physical contact between the conductive gel and the male snap. The only flexible conductor disclosed in U.S. Pat. No. 3,977,392 is a thin silver foil strip about 1¼ inches long and 3/16 inch wide.

It is an object of the invention to provide an improved strain relief coupling assembly for an electrode.

Another object is to provide a strain relief coupling assembly which permits releasable attachment of an electrode with minimal disturbance to a primary electrical signal coupler.

Another object of the invention is to provide relief of strain caused by patient movements on a wire connecting a monitoring device to an electrode.

SUMMARY OF THE INVENTION

In accordance with the present invention, electrical noise is minimized when a strain relief pad and an elongated flexible electrical coupler containing slack is positioned between the monitoring device and a conventional gel-containing electrode-to-skin coupling. In one embodiment, a connector element on a separate adhesive pad is added to the circuit, between the monitoring device and the electrode which establishes electrical contact with the patient's skin. The connector element is conductively attached to the electrode-to-skin coupling through an elongated flexible electrically conductive element, and to the monitoring device through a lead extending from that device. In accordance with the invention, the flexible conductive element of the strain relief pad contains sufficient slack to provide strain relief by physically isolating the electrode-to-skin coupling from the lead from the monitoring device, as described in more detail below.

Specifically, in one embodiment the present invention provides a strain relief (SR) coupling assembly for an electrode having an electrode connector element affixed to one end thereof, comprising: a) a first sheet element being electrically non-conductive and having top and bottom surfaces and having an adhesive layer on said bottom surface; b) a pad connector element affixed to said top surface, said pad connector element being reversibly engageable with said electrode connector element; c) an elongated flexible electrically conductive element connected at one end to said pad connector element and at its opposite end to an SR connector element. In another embodiment, the SR coupling assembly of the invention further includes a second adhesive backed, electrically nonconductive sheet element bearing an electrically conductive connection (such as a gel) on its underside, with a feed-through conductive element connected to the aforementioned flexible conductive element. In yet another embodiment, the second sheet element may be detachably connected to the first sheet element. In another embodiment, the second sheet element may be connected to the first sheet element by an elongated flexible, electrically nonconductive connecting sheet element underlying and supporting the flexible conductive element.

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENTS

Figure 1:
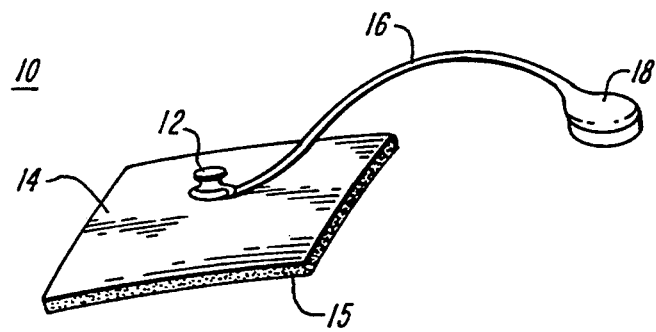
FIG. 1 shows one embodiment of the strain relief coupling assembly of the invention.

In the embodiment set forth in FIG. 1, the invention comprises a strain relief (SR) coupling assembly 10 including a pad connector element such as a male snap connector 12 affixed to the top surface of an electrically nonconductive first sheet element 14 disposed about the pad connector element. Preferably, element 14 is flexible, but not necessarily so. The pad connector element is reversibly engageable with an electrode connector element on a wire or lead from the monitoring device. On its underside, the first sheet element 14 is coated with a layer of biologically compatible adhesive layer 15 as are known in the art. Prior to use, the adhesive layer 15 may be covered with a release sheet which preserves the adhesive layer 15 for use on the patient. The release sheet may be of waxy paper, or of thin plastic, or the like. The first sheet element 14 does not allow electrical contact to be made between the patient's skin and the pad connector element 12. An elongated flexible electrically conductive element 16 is connected at one end to pad connector element 12 and at its opposite end to SR connector element 18, which may be a female snap connector. The elongated flexible electrically conductive element 16 is of sufficient length that slack may be maintained therein when the SR coupling assembly is in operation. The elongated flexible electrically conductive element 16 may be made of any suitable conductive material and may be in the form of a wire, a ribbon conductor, or the like. The elongated flexible electrically conductive element is preferably coated with a non-conductive insulating material. In accordance with the invention, the elongated flexible electrically conductive element may be permanently affixed to the pad connector element 12, or it may be removably affixed to pad connector element 12. Methods for effecting such permanent and removable connections between pans of electrical circuits are known to those of skill in the art.

Figure 2:
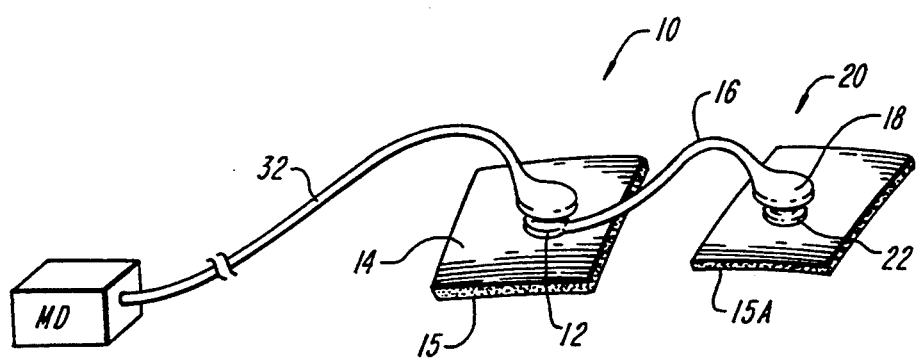
FIG. 2 depicts the strain relief coupling assembly of FIG. 1 in operative association with an electrode.

The SR coupling assembly of FIG. 1 may be used, for example, as set forth in FIG. 2. A conventional monitoring electrode assembly 20 is affixed to the patient in the normal manner. Such monitoring electrode assemblies are commercially available and are exemplified by the 3M Red Dot TM electrode provided by Minnesota Mining and Manufacturing Co., or the Medi-Trace TM electrode provided by Graphic Controls of Buffalo, N.Y., or the CarboCone® electrode distributed by Lynn Medical Instrument Co. of Bloomfield Hills, Mich. Such electrodes are generally supplied with solid or liquid conductive gel preapplied under an electrode connector element 22 such as a male snap, the gel being protected from drying with a removable cap or sheet and are commonly designated as "adhesive pregelled electrodes." After removal of the protective cap or sheet, the monitoring electrode assembly 20 is affixed to the patient through the adhesive pad of the electrode assembly. The SR coupling assembly 10 of the invention is also affixed to the patient's skin near the monitoring electrode assembly 20, using the contact adhesive on the underside of the first sheet element 14. If desired, the SR coupling assembly 10 may be affixed to the patient near the site to be monitored prior to affixation of the monitoring electrode.

In accordance with the invention, the SR coupling assembly 10 must be affixed at such a distance from the monitoring electrode assembly 20 that slack is maintained in the elongated flexible electrically conductive element 16. Elongated flexible electrically conductive element 16 must not be stretched tightly between the pad connector element 12 of the SR coupling assembly and the electrode connector element 22. Slack is preferably defined in accordance with the invention as a loose loop in the elongated flexible electrically conductive element 16 when both the first sheet of the SR coupling assembly and the monitoring electrode assembly are affixed to the patient and the electrical connections between the monitoring device, the SR coupling assembly, and the monitoring electrode assembly are completed.

The SR connector element 18 of the SR coupling assembly 10 is connected to the electrode connector element 22 of the monitoring electrode assembly 20, maintaining slack in the elongated flexible electrically conductive element 16 as set forth above. A lead 32 from a monitoring device (MD) includes a monitoring device connector 30 at its distal end, which is coupled to the pad connector element 12 of the SR coupling assembly 10. With this configuration, the slack in the elongated flexible electrically conductive element 16 mechanically decouples the conductive gel from patient-induced motion of the lead, while maintaining a high reliability electrical connection.

Figure 3:
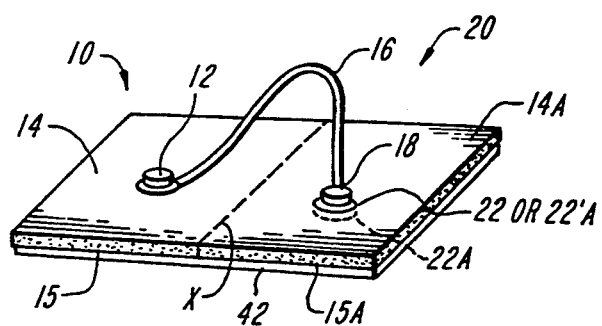
FIGS. 3–5 show alternative forms of the invention.

In accordance with the present invention, a second sheet element 14A may be provided in combination with the first sheet element 14 described above. Preferably, sheet 14A is flexible, but not necessarily so. In this embodiment, as shown in FIG. 3, the second sheet element 14A has top and bottom surfaces and includes an electrical feed-through conductor 22A extending between those surfaces, and an electrically conductive gel element (not shown) adjacent to its bottom surface for establishing electrical contact with the skin. The bottom surface of the pad element is coated with an adhesive layer 15', in a manner similar to the bottom surface of the first sheet element 14. The top surface of the second sheet element 14A contains a connector element 22 which may be permanently connected to first sheet element through the elongated flexible conductive element 16. Alternatively, the connection between connector element 22 and first pad connector element 12 may be releasable, through a connector element 22' such as a male snap connector. The connector element 22 or 22' is connected to the electrical feed-through conductor 22A. As above, an electrically conductive gel is supplied preapplied to the electrical feed-through conductor 22A, with a removable cap or sheet to protect the gel from drying. In this embodiment, the SR connector is affixed to the top surface of the second sheet element and an electrical connection is maintained from the patient's skin through the conductive gel element beneath the second sheet element 14A, through the connector element 22A, through the SR connector 22', through the elongated flexible electrically conductive element 16, through the first pad connector element 12, through the electrode connector element 30, through the wire or lead 32 to the monitoring device. When in use, slack as defined above is maintained between the first and second sheet elements in order to provide mechanical separation between the conductive gel and the monitoring device.

In accordance with the present invention, the second sheet element may optionally be affixed to the first sheet element. Such affixation may occur through a perforation X (depicted as a broken line in FIG. 3) in an otherwise contiguous first sheet element and second sheet element, as depicted in FIG. 3. In the electrode assembly embodiment set forth in FIG. 3, the SR coupling assembly 10 includes detachably connected sheets 14 and 14A, having adhesives 15 and 15A on their respective bottom surfaces. A release sheet 42 is shown affixed to the underside of sheets 14 and 14A, which release sheet can be removed without altering the characteristics of the adhesive layers 15 and 15A. In use, the SR coupling 10 and the monitoring electrode 20 are detached from each other by tearing along perforations X. SR coupling assembly 10 and monitoring electrode 20 are pulled apart from each other, and the portion of sheet 42 affixed to the underside of monitoring electrode 20 is removed. Monitoring electrode 20 is adhesively affixed to the patient at the site to be monitored. The remaining portion of sheet 42 is removed from the SR coupling assembly 10, and SR coupling assembly 10 is affixed to the patient at a site removed from the site of the monitoring electrode but sufficiently close to allow slack in elongated flexible electrically conductive element 16 to be maintained when SR connector element 18 is reattached to electrode connector element 22. Monitoring device connector 30 on external lead wire 32 extending to the monitoring device is coupled to pad connector element 12 of SR coupling assembly 10, maintaining the slack-containing configuration which mechanically decouples the lead wire from patient-induced motion of the conductive gel.

Figure 4:
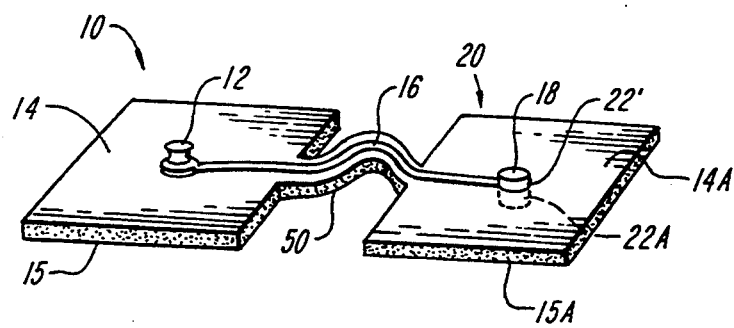

In yet another embodiment, as shown in FIG. 4, the first sheet 14 containing the SR coupling assembly and the second sheet 14A containing the skin electrode connector element, with the elongated flexible electrically conductive element 16 affixed therebetween as described above, may be connected by an elongated flexible connecting sheet element 50. The elongated flexible electrically conductive element 16 may extend along and be affixed to the elongated flexible connecting sheet element 50, or alternatively the elongated flexible electrically conductive element 16 may be substantially free of the elongated flexible connecting sheet element. This embodiment may optionally include a release sheet element as described above.

Figure 5:
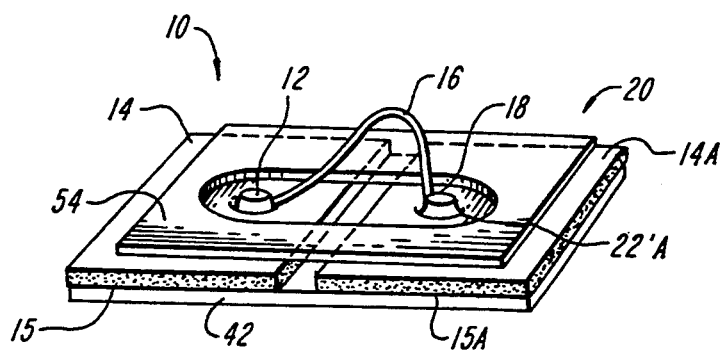

Another embodiment is shown in FIG. 5. That embodiment is similar to the embodiment in FIG. 2 with a release sheet 42 affixed to the adhesive-bearing bottom surfaces of sheets 14 and 14A and with an adhesive-bearing sheet 54 releasably affixed to the top of sheets 14 and 14A. With this configuration, the sheet 42 may first be removed and the sheets 14 and 14A affixed to the patient, with the spaced apart relation of those sheets maintained (to ensure affixation with slack in conductor 16) by the action of sheet 54. That sheet 54 may subsequently be removed.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A strain relief (SR) coupling assembly for an electrode having an electrode connector element affixed to one end thereof, comprising:
   A. a first sheet element being electrically non-conductive and having top and bottom surfaces and having an adhesive layer on said bottom surface,
   B. a pad connector element affixed to said top surface, said pad connector element being reversibly engageable with said electrode connector element, and said pad connector element being electrically isolated from said bottom surface, and C. an elongated flexible electrically conductive element connected at one end to said pad connector element and at its opposite end to a SR connector element.

2. A strain relief coupling assembly according to claim 1 wherein said SR connector element is reversibly engageable with said pad connector element.

3. A strain relief coupling assembly according to claim 1 further comprising:
   i. an electrically conductive gel element,
   ii. a second sheet element having top and bottom surfaces, and including an aperture containing said electrically conductive gel element, said aperture being surrounded by an adhesive layer on the said bottom surface, and wherein said SR connector element is affixed to said top surface of said second sheet element and is electrically connected to said gel element.

4. A strain relief coupling assembly according to claim 3, further comprising a perforated sheet connecting said first sheet element and second sheet element.

5. A strain relief coupling assembly according to claim 4, further comprising a release sheet releasably affixed to said adhesive layers on said bottom surfaces of said first sheet element and said second sheet element, whereby said first sheet element and said second sheet element are held in a spatial relationship with said flexible electrical conductive element being slack.

6. A strain relief coupling assembly according to claim 3, further comprising an elongated flexible connecting sheet element connecting said first sheet element and said second sheet element.

7. A strain relief coupling assembly according to claim 6, further comprising a release sheet releasably affixed to said adhesive layers on said bottom surfaces of said first sheet element and said second sheet element, whereby said first sheet element and said second sheet element are held in a spatial relationship with said flexible electrical conductive element being slack.

8. A strain relief coupling assembly according to claim 7, further comprising a third sheet element having top and bottom surfaces and having an adhesive layer on said bottom surface, said third sheet element being disposed so that its adhesive layer is releasably attached to said top surfaces of said first sheet element and said second sheet element.

9. A strain relief coupling assembly according to claim 6 wherein said elongated flexible electrically conductive element extends along and is affixed to said connecting sheet element.

10. A strain relief coupling assembly according to claim 9, further comprising a release sheet releasably affixed to said adhesive layers on said bottom surfaces of said first sheet element and said second sheet element, whereby said first sheet element and said second sheet element are held in a spatial relationship with said flexible electrical conductive element being slack.

11. A strain relief coupling assembly according to claim 10, further comprising a third sheet element having top and bottom surfaces and having an adhesive layer on said bottom surface, said third sheet element being disposed so that its adhesive layer is releasably attached to said top surfaces of said first sheet element and said second sheet element.

12. A strain relief coupling assembly according to claim 3, further comprising a release sheet releasably affixed to said adhesive layers on said bottom surfaces of said first sheet element and said second sheet element, whereby said first sheet element and said second sheet element are held in a spatial relationship with said flexible electrical conductive element being slack.

13. A strain relief coupling assembly according to claim 12, further comprising a third sheet element having top and bottom surfaces and having an adhesive layer on said bottom surface, said third sheet element being disposed so that its adhesive layer is releasably attached to said top surfaces of said first sheet element and said second sheet element.

* * * * *